United States Patent [19]

Efstathiou et al.

[11] Patent Number: 5,928,913
[45] Date of Patent: Jul. 27, 1999

[54] VECTORS FOR GENE DELIVERY

[76] Inventors: Stacey Efstathiou, 18 Norwich Street, Cambridge, United Kingdom, CB2 1NE; Stephen C. Inglis, 2 Rhugarye Gardens, Linton, Cambridge, United Kingdom, CB1 6LX; Xiaoliu Zhang, 21 Oak Tree Avenue, Cambridge, United Kingdom, CB4 1AZ

[21] Appl. No.: 08/621,501

[22] Filed: Mar. 25, 1996

Related U.S. Application Data

[60] Provisional application No. 60/000,029, Jun. 8, 1995.

[30] Foreign Application Priority Data

Mar. 23, 1995 [GB] United Kingdom .................... 9505892

[51] Int. Cl.$^6$ .............................. C12N 15/63; C12N 5/08; C07H 21/04
[52] U.S. Cl. .................................... 435/172.3; 435/320.1; 435/372.3; 536/23.1; 536/23.5; 536/23.72
[58] Field of Search ............................... 424/93.21, 93.3, 424/204.1, 196.11, 225, 229.1; 435/69.1, 91.33, 235.1, 240.2, 320.1, 172.3, 372.3; 514/44, 806; 530/350, 806; 536/23.1, 23.5, 23.72

[56] References Cited

U.S. PATENT DOCUMENTS

| 4,996,152 | 2/1991 | Carter et al. ........................ | 453/172.3 |
| 5,501,979 | 3/1996 | Geller et al. ........................ | 435/320.1 |

FOREIGN PATENT DOCUMENTS

| 92 05263 | 4/1992 | WIPO . |
| 92 07954 | 5/1992 | WIPO . |
| 9303743A1 | 3/1993 | WIPO . |
| 94 04695 | 3/1994 | WIPO . |
| 94 21807 | 9/1994 | WIPO . |

OTHER PUBLICATIONS

Nguyen et. al.. Replicatin–defective mutants of Herpes Simplex Virus (HSV) induce cellular immunity and protect against lethal HSV infection. J. Virol.. vol. 66(12):7067–7072, Nov. 18, 1992.

Efstathiou et. al.. Role of Herpes Simplex Virus type I thymidine kinase in pathogenesis. J. Gen. Virol.. vol. 70:869–879, Apr. 25, 1989.

West et al. Gene expression in adeno–associated virus vectors: The effects of chimeric mRNA structure, helper virus, and adenovirus VA1 RNA. Virol. vol. 160:38–47, Jan. 1987.

Tratschin et al. A human parvovirus. adeno–associated virus, as a eucaryotic vector: transient expression and encapsidation of the procaryotic gene for chloramphenicol acetyltransferase. Mol. and Cell. Biol. vol. 4(10):2072–2081, Oct. 1984.

Weatherall, D.J. Scope and limitations of gene therapy. British Med. Bull. vol. 51(1):1–11, Jan. 1995.

Verma et al. Gene therpay– Promises, problems and prospects. Nature. vol. 389:239–242, Sep. 18, 1997.

Orkin et al. Report and recommendations of the panel to assess the NIH investment in research on gene therapy, Dec. 7, 1995.

Lowenstein, et al., "Simultaneous Detection of Amplicon and HS–1 Helper Encoded Proteins Reveals that Neurons and Astrocytoma Cells do Express Amplicon–Borne Transgenes in the Absence of Synthesis of Virus Immediate Early Proteins", Molecular Brain Research, 30(1):169–175 (1995).

Wu, et al., "Examination of Conditions Affecting the Efficiency of HSV–1 Amplicon Packaging", J. Virol. Methods, 52:219–229 (1995).

Lowenstien, et al., "Herpes Simplex Virus 1 (HSV–1) Helper Co–Infection Affects the Distribution of an Amplicon Encoded Protein in Glia", NeuroReport, 5(13):1625–1630 (1994).

Frenkel, et al., "Minireview the Herpes SImplex Virus Amplicon—a Versatile Defective Virus Vector", Gene Therapy, 1:S40–S46 (1994).

Craig, et al., "Use of HSV–1 Amplicon Vectors to Study RNA and Protein Targeting in Cultured Hippocampal Neurons", Gene Therapy, 1:S72 (1994).

Kaplitt, et al., "Expression of a Functional Foreign Gene in Adult Mammalian Brain Following In Vivo Transfer Via a Herpes Simplex Virus Type 1 Defective Viral Vector", Mol. Cell. Neurosciences, 2:320–330 (1991).

Kwong, et al., "The Herpes Simplex Virus Amplicon IV. Efficient of a Chimeric Chicken Ovalbumin Gene Amplified Within Defective Virus Genomes", Virology, 142:421–425 (1985).

Spaete, et al. "The Herpes Simplex Virus Amplicon Analyses of CIS–Acting Replication Functions", Proc. Natl. Acad. Sci. USA, 82:694–698 (1985).

Kwong, et al., "Herpes Simplex Virus Amplicon Effect of Size on Replicon of Constructed Defective Genomes containing Eucaryotic DNA Sequences", J. Virology, 51(3):595–603 (1984).

Spaete, et al., "The Herpes Simplex Virus Amplicon a New Eucaryotic Defective– Virus Cloning–Amplfying Vector", Cell, 30:295–304 (1982).

(List continued on next page.)

*Primary Examiner*—James Ketter
*Assistant Examiner*—William Sandals
*Attorney, Agent, or Firm*—Flehr Hohbach Test Albritton & Herbert LLP; Walter H. Dreger; Robin M. Silva

[57] ABSTRACT

Herpesvirus amplicon preparations comprise an origin of replication, a packaging sequence, and at least one inserted gene under control of a promoter, suitable for use as an immunogen or vaccine, in association with helper herpesvirus or DNA, wherein the associated helper virus is of restricted replication competence in a normal host cell; for example where the associated helper virus has an inactivating defect in respect of a gene essential for production of infectious new virus particles, and where the amplicon carries an inserted gene necessary for the propagation of the helper virus.

17 Claims, No Drawings

OTHER PUBLICATIONS

Leib, et al., "Is Herpes Simplex Virus the Right Tool for the Job?", Bioassays, 15(8):547–554 (1993).

Geller, et al., "An Efficient Deletion Mutant Packaging System for Defective Herpes Simplex Virus Vectors Potential Applications to Human Gene Therapy and Neuronal Physiology", Proc. Natl. Acad. Sci., 87:8950–8954 (1990).

Glover, et al., "Expression Using a Defective Herpes Simplex virus (HSV–1) Vector System", DNA Cloning 4, Oxford University Press: New York, pp. 263–283 (1995).

Lim, et al., "Generation of High–Titer Defective HSV–1 Vectors Using an IE 2 Deletion Mutant and Quantitative Study of Expression in Cultured Cortical Cells", Biotechniques, 20(3):460–469 (1996).

Berthomme, et al., "Increased Transcomplementation Properties of Plasmid Carry HSV–1 Origin of Replication and Packaging Signals", Virology, 216(2):437–443 (1996).

VECTORS FOR GENE DELIVERY

This application claims the benefit of Provisional Application No. 60/000,029, filed Jun. 8, 1995.

FIELD OF THE INVENTION

This invention relates to amplicon vectors for gene delivery, and to their uses as immunogens, vaccines, vaccine adjuvants, immunotherapeutic agents, and as agents in gene therapy. The invention also relates to their uses in diagnostic procedures, both in vivo and in vitro, and to their use for the ex-vivo or in-vitro preparation of derivative biological materials for immunogenic and other purposes as already mentioned. The invention also relates to processes and materials for producing and propagating such vectors and their derivatives.

BACKGROUND OF THE INVENTION, AND PRIOR ART

Numerous techniques are known for introducing DNA into eukaryotic cells, often by means of vectors, and often in the form of nucleic acid encapsidated by a (frequently virus-like) proteinaceous coat.

Many such techniques have been proposed, and some used, for a wide range of clinical as well as experimental applications.

The deliberate introduction of DNA encoding a desired gene, under conditions where the gene may be expressed within the cell and leads to the production of RNA and/or protein, can be desirable in order to provoke any of a wide range of useful biological responses.

It has recently been reported that injection even of free (naked) plasmid DNA directly into body tissues such as skeletal muscle or skin can lead to protein expression and to the induction of cytotoxic T lymphocytes (CTLs) and antibodies against the encoded protein antigens contained in the plasmid (Ulmer et al, Science, 259 (1993) 1745–1749; Wang et al, Proc Nat Acad Sci U.S. 90 (1993), 4157–4160; Raz et al, Proc Nat Acad Sci U.S. 91 (1994), 9519–9523). Nevertheless, the efficiency of nucleic acid introduction by virus-like vectors can often be higher than the effect of naked DNA and there are continuing efforts to identify and make improved virus-like vectors.

Among known virus vectors are recombinant viruses, of which examples have been disclosed based on several virus classes including poxviruses, herpesviruses, adenoviruses, and retroviruses. Such recombinants can carry heterologous genes under the control of promoters able to cause their expression in vector-infected host cells. Recombinant viruses of the vaccinia and other types are mentioned and cited for example in a review by Mackett, Smith and Moss (J Virol 49(3) (1994) 857–864).

By way of further example, specifications WO 88/00971 (CSIRO. Australian National University: Ramshaw et al), and WO 94/16716 (Virogenetics Corp: Paoletti et al) describe recombinant vaccinia viruses carrying genes for a variety of cytokines, e.g. GMCSF, and reported effects include potentiation of the immune response to recombinant viruses carrying cytokine genes.

Examples of further known recombinant virus vectors, for example of the vaccina virus and herpes virus types, are disclosed in specifications WO 92/16636 (Cantab Pharmaceuticals: Boursnell et al) and WO 92/05263 (Immunology Ltd: Inglis et al) and WO 94/21807 (Cantab Pharmaceuticals: Inglis et al), where recombinant viruses are disclosed that carry genes for heterologous antigens intended to evoke an immune response in a treated subject.

The prior art also includes amplicons based on herpes viruses such as herpes simplex virus, as described for example by Vlazny and Frenkel, in Proc Nat Acad Sci U.S. 78 (1981) 742–746; and by R. R. Spaete and N. Frenkel, Cell 30 (1982) 295–304. Such amplicons are in effect DNA which is highly defective in respect of viral gene functions, but contains at least a copy of a HSV origin of replication (ORIs) and a packaging signal sequence (localised in the repeated 'a' sequence of the HSV genome). When introduced into suitable cells together with a helper HSV virus, the amplicons can propagate in dependence upon propagation in the same cells of the helper herpes viruses, which provide trans replication and packaging functions (including structural components of the virions in which progeny amplicons are packaged) not encoded by the amplicons themselves.

Specification WO 94/04695 (Rockefeller University; M. G. Kaplitt) relates to a herpesvirus defective vector carrying a foreign gene 'driven' by a promoter endogenous to a host that is to be infected by the vector. The prospective uses are stated to include gene therapy e.g. in connection with adult mammalian brain. In related publications, Kaplitt et al, in Proc Nat Acad Sci U.S. 91(19) (1994) 8979–8983 (and an earlier article) discuss the use of a defective herpes simplex virus vector to express a foreign gene in the adult rat brain. They describe a herpes simplex virus amplicon containing a foreign gene (bacterial lacZ) downstream of a 2.7 kb fragment of rat preproenkephalin promoter.

U.S. Pat. No. 4,996,152 (J. K. Carter et al; U.S. Sec of Agriculture) describes DNA fragments (seeds) having the characteristics of amplicons from Marek's disease virus, of which concatemers of the seeds and associated genes were described as having potential as vaccines or delivery vectors when cotransfected and replicated in the presence of helper viruses, and for use for inserting genes into the helper viruses.

A. I. Geller et al, in Proc Nat Acad Sci (1990) (Nov) 87:8950–8954 describe "An efficient deletion mutant packaging system for defective herpes simplex virus vectors; Potential applications to human gene therapy and neuronal physiology", based on use of a defective HSV1 vector system to introduction E. coli beta-galactosidase into in cells from adult rat brain, propagated in association with a helper virus deleted in respect of gene IE3, on a complementing cell line.

"Gene therapy" includes the clinical aim of replacing the function of a gene which is missing or defective, and attempts are known to treat cystic fibrosis or adenosine deaminase (ADA) deficiency by introducing into patient cells functional copies of the genes defective in these diseases (i.e. genes encoding CFTR and ADA respectively).

Another known proposal for a form of gene therapy comprises introducing a nucleic acid sequence to up-regulate or down-regulate expression of a target gene in the host cell, either by means of a protein encoded by the introduced nucleic acid sequence or by means of an antisense relation between RNA encoded by the introduced nucleic acid and a target nucleic acid molecule corresponding to an endogenous gene product.

Traditionally the aim of vaccination was to protect against infectious diseases, but this aim has now broadened to include other kinds of immune stimulation, for example to include treatment of tumours and some other immune diseases, and to include therapy as well as prophylaxis (prevention).

It remains desirable to provide further forms and preparations of vectors that show useful combinations of desirable properties in connection with gene delivery e.g. for purposes such as gene therapy and vaccination.

THE PRESENT INVENTION

The aims of the invention include the provision of amplicon-based vectors, that can be used as immunogens, such as vaccines or vaccine adjuvants, and/or in the preparation of immunogene e.g. in connection with ex-vivo treatments. Certain examples of the vectors can be used for therapeutic or prophylactic corrective gene therapy.

The aims of the invention also include the provision of preparations of amplicons that can be more safely administered to subjects of treatment than known amplicon preparations would be.

The aims of the invention also include the provision of amplicon-based vectors for gene delivery that can be propagated in culture with satisfactory yield of viral-packaged amplicon compared to helper-virus, especially for example where the amplicon carries an inserted gene necessary for the propagation of the helper virus at least under the chosen culture conditions. Such as system, for example as described below, can give an important benefit in relative yield of amplicon compared to helper virus.

Also included among the aims of the invention is the provision of vectors carrying genes that can usefully encode multiple antigens, e.g. of highly mutable or of antigenically variable pathogens.

According to the invention there is provided a preparation of a herpesvirus amplicon comprising an origin of replication, a packaging sequence, and at least one inserted gene under control of a promoter, suitable for use as an immunogen or vaccine, in association with helper herpesvirus or DNA thereof, wherein the associated helper virus is of restricted replication competence in a normal host cell.

Also provided by the invention is a preparation of a herpesvirus amplicon comprising an origin of replication, a packaging sequence, and at least one inserted gene under control of a promoter, in association with a helper virus or DNA thereof, wherein the associated helper virus has an inactivating defect in respect of a gene that is essential for the production of infectious new virus particles, such that the helper virus cannot cause production of infectious new virus particles expect when said virus infects recombinant complementing host cells which have been made to carry and can express a gene that provides the function of said essential viral gene; and wherein the amplicon carries an inserted gene necessary for the propagation of the helper virus.

In connection with the present invention, the terms 'amplicon' and 'packaged amplicon' are used (where the context permits) to mean:

nucleic acid encoding (in sequence) an origin of replication, such as a viral origin of replication, e.g. a herpesvirus origin of replication; a packaging signal such as a viral packaging signal, e.g. a herpesvirus packaging signal; and an open reading frame defining a gene, often a heterologous gene, under control of a transcriptional promoter that is active in a host cell to be infected by the amplicon; this sequence of elements optionally being present in plural concatenated copies, and the nucleic acid often being packaged in a viral coat that is functionally effective to enable introduction of the nucleic acid of the amplicon into a host cell within the normal host range of the virus corresponding to the viral coat. The whole packaged amplicon can function as a highly defective virus, and is dependent, for its propagation in a culture system to yield new amplicons, on the presence in the same host culture cell of a co-infecting helper virus of the type corresponding to the amplicon, which is usually replication-competent under the conditions of the culture.

Such an amplicon amounts to a highly defective viral vector, having a nucleic acid sequence that lacks a plurality of genes encoding proteins necessary to the functions of replicating and/or packaging the vector nucleic acid, often indeed lacking a majority or all of such genes. Such amplicons can for example be based on adaptations of the constructs mentioned in R. Spaete et al, Cell 30 (1982) 295–304, engineered to carry inserted genes; or on adaptations of other prior descriptions of amplicons as mentioned herein.

Other aims of the invention will also be apparent from the present description: the invention also includes the use of replicons of various herpesviruses, carrying inserted genes, as mentioned below. In particular the invention also extends to packaged and unpackaged amplicon preparations, e.g. as vectors encoding selected genes of interest; to corresponding amplicon DNA and plasmids comprising said amplicon DNA; to mixed preparations of amplicons with helper virus or helper virus DNA; including amplicon preparations that are in a state of substantial biological purity, e.g. either a DNA or as packaged amplicons in association with helper virus; to biologically isolated amplicon preparations (usually containing helper virus but free of other unwanted contaminants), and to formulations of the amplicons in pharmaceutically acceptable form with pharmaceutically acceptable carriers; and to methods of propagation and production and methods of use of the amplicon preparations as vectors for gene delivery and otherwise.

In many examples, such defective viral vectors contain no viral genes, and are entirely or almost entirely dependent on the helper virus for all virally encoded gene products.

In other examples, the defective viral vectors can encode for example one or two, (or up to four or five) viral genes in respect of which the helper virus has been selected as a deletant or inactivated mutant.

The genes of the helper virus and the defective virus vector taken together may encode either all viral functions, or may (preferably) be defective in respect of one or more defined viral functions, which can be provided by a recombinant complementing host cell line used for the propagation of the amplicon.

Amplicons propagated with replication-defective helper virus

In one aspect, therefore, the present invention provides a preparation of a vector for gene delivery, comprising amplicons that carry at least one gene desired to be delivered to a eukaryotic cell when the amplicon is used as a vector, wherein the amplicons are dependent upon a helper-virus for their propagation, but the preparation is preferably free from any helper-virus particle that is replication-competent in normal host cells.

'Normal host cells' means non-recombinant cells of an animal within the normal host range of the virus on which the amplicon is based, or of the helper virus, i.e. cells that are not supplemented with heterologous genes of viral origin, in contrast with recombinant cells carrying a gene that complements an artificial deletion in a virus.

Such preparations usually also contain helper-virus particles: such helper virus particles can consist of genetically-disabled virus of the kind described in specification WO 92/05263 and WO 94/21807, i.e. mutant virus that lacks at least one gene essential for the production of infectious new virus particles when the mutant virus infects a normal host cell. Thus the genome of the helper virus can be a mutant virus genome which has an inactivating defect in respect of a selected gene essential for the production of infectious new virus particles by infected host cells, such that the virus can infect normal host cells (i.e. cells other than those which have been mutated so that they express the product of the essential gene in respect of which the virus is defective) and cause viral replication and expression of viral antigen genes in those cells, but cannot cause production of normal infectious virus. In such a mutant virus the genetic defect can be such (e.g. deletion of essential glycoprotein gene such as herpesvirus gH or gO or homologue thereof) as to allow the production and release of non-infectious viral particles when the mutant virus infects host cells other than such recombinant complementing host cells.

The amplicons together with helper virus can be propagated on a culture of a complementing host cell line, i.e. a genetic recombinant host cell line that carries and can express a gene that complements the function of the essential viral gene in respect of which the helper virus is defective.

Such genetically-disabled (helper) viruses are replication-competent in complementing host cells of the recombinant host cell line, but they are replication-incompetent, i.e. multiplication-incompetent, in ordinary (normal) host cells, and do not product there any infectious progeny virus particles. Replication-incompetence, or multiplication-incompetence, in this sense, does not exclude that the genetically-disabled virus causes some intracellular viral molecular replication events to take place in normal host cells infected therewith. The mutation giving rise to the genetic disability is indeed preferably in such an essential gene (as for example a gene for an envelope glycoprotein needed for infectivity, or other 'late' gene), that intracellular molecular replication of many or even most virally-encoded products such as nucleic acids and proteins does take place in a normal host cell, although no infectious new virus particles are ultimately formed thereby.

In certain embodiments, the invention therefore provides amplicon preparations having an important advantage, that even where, as is usual, they include helper virus, they do not generate infectious new virus particles, nor freely propagate in a normal host cell or host animal, and they do not spread spontaneously from a treated host animal to other untreated host animals.

Amplicons and helper viruses provided and used in connection with this invention can be based on human or veterinary (non-human animal) herpesviruses, and especially on herpex simplex virus of type 1 or type 2, human cytomegalovirus, Epstein-Barr virus, varicella zoster virus, or on pseudorabies virus, bovine herpes virus, equine herpesvirus, or Marek's disease virus.

The genetically disabled viruses can be based on the deletion or inactivation of any gene that is essential for the production of infectious new virus particles when such virus infects a normal host cell. Fully essential genes can for example be identified by the occurrence of conditional-lethal temperature-sensitive mutations in them. In herpes simplex viruses, essential genes such as for example gB, gD, gH, gL, ICP4, ICP8 and/or ICP27 can be deleted or otherwise inactivated. In other herpesviruses, known essential genes, such as any known essential homologous to the above-mentioned genes of HSV, can be selected for deletion or other inactivation. Cytomegalovirus can for example be genetically disabled by deleting or otherwise inactivating genes responsible for temperature-sensitive mutations, for example as identifiable from Dion et al, Virology 158 (1987) 228–230.

Preferred genes for deletion are those such as gH, gB, or gL, or their equivalents, that code for essential viral glycoproteins or other viral protein that forms part of the virion structure and is essential for infectivity of progeny virus particles.

Corresponding complementing recombinant host cell lines can be made in ways analogous to the construction of a complementing host cell line as described below or in specification WO 92/05263, adapted by sourcing a copy of the gene to be deleted from the chosen virus to be genetically disabled.

Amplicons carrying genes needed by helper virus

In a further aspect, the present invention provides a preparation of a vector for gene delivery, comprising viral-packaged amplicons that carry at least one gene desired to be delivered to a eukaryotic cell when the amplicon is used as a vector, the amplicons being dependent upon a helper-virus for their propagation, and the preparation usually also containing helper-virus particles: wherein the amplicons also carry a helper gene that is necessary to the propagation of helper-virus, at least under certain culture conditions, and wherein the helper-virus particles are genetically defective in respect of that helper gene or in respect of a functionally equivalent viral gene.

The helper virus can be a genetically-disabled virus of the kind described above (see also specification WO 92/05263 and 94/21807). Embodiments of the invention as described below relate to herpesvirus amplicon vectors.

In certain embodiments, the amplicon can encode a gene for a function that can be needed for helper virus replication, so that it can be propagated in a host cell culture under conditions where the amplicon is essential to propagation of the helper virus, as well as vice versa. For example the amplicon can carry an inserted TK gene, the helper virus is TK-and is also a deletant in respect of an essential viral glycoprotein, whereby the amplicon is necessary for the propagation of the helper virus when the preparation is grown on TK-cells in the presence of methotrexate. The genes of the helper virus and the defective virus vector taken together can be defective in respect of an essential viral gene function. The amplicon can carry an inserted first essential viral gene, the helper virus being a deletant in respect of the corresponding first essential viral gene and is also a deletant in respect of a second essential viral gene, whereby the amplicon is necessary for the propagation of the helper virus when the preparation is grown on cells complemented in respect of the function of the second essential viral gene. The first essential viral gene can encode an essential viral glycoprotein and the second essential viral gene also can encode an essential viral glycoprotein (different from that encoded by the first essential viral gene): e.g. gO and gH respectively.

An example of such a preparation is a preparation in which herpesvirus amplicons carry (a) a gene which it may be desired to deliver to a eukaryotic cell when the amplicon is used as a vector, and (b) a thymidine kinase gene; and the helper-virus comprises a thymidine-kinase-deficient mutant herpes simplex virus.

Such a preparation can be propagated in culture on host cells using a thymidine-kinase-negative helper virus in the presence of methotrexate, which renders the propagation of helper-virus dependent on thymidine kinase. Methotrexate imposes a metabolic block on herpesvirus replication unless thymidine kinase is present. Selection on this basis requires the use of a thymidine-kinase-deficient cell line. In a cell infected both by amplicon and by replication-competent helper virus, virions are generally produced which contain either amplicon nucleic acid, or helper-virus nucleic acid. Cells infected by helper-virus can alone produce only helper-virus, and not amplicon. In the embodiment under discussion, where the thymidine kinase is provided by expression of a TK gene carried by the amplicon, the TK-negative helper-virus is replication-competent, and can propagate, only in host cells that are also infected with amplicon. Thus the proportion of helper-virus that would otherwise propagate in cells not infected by amplicon and multiply without assisting the propagation of amplicon, can by this arrangement be reduced or eliminated.

An advantage of this arrangement is that an amplicon preparation can be propagated in a suitable host cell culture under conditions where the amplicon is essential to propagation of the helper virus, as well as vice versa, with improved yield of amplicons compared to culture under conditions where the helper gene is not essential or where the helper virus is not so defective.

Thus, for example, the helper virus can be a TK–, gH– herpes virus such as a simplex virus; the amplicon can carry a TK gene as well as a gene intended to be delivered to a eukaryotic cell when the amplicon is used as a vector: and the complementing host cell line can carry and express a gH gene.

Instead of a TK+ amplicon and TK– helper virus, the amplicon can be made to carry for example some other gene that is essential to the replication of helper virus, and the helper virus can be made defective in respect of that gene, for example another essential viral glycoprotein gene, e.g. the gene for glycoprotein gB, gD or gL.

Often it is preferred that the amplicon should not be made to carry in such a case a sole essential gene that has been deleted in order to provide genetic disability in the helper virus which is a virus according to specification WO 92/05263, cited above, though this can be done. A defect in the helper virus that is complemented by the amplicon is thus preferably different from, and additional to, the defect present in the essential gene of the helper virus that is to be complemented by a complementing cell line to be used for propagation of the amplicon preparation.

For increased safety in use, the helper herpes virus can if desired be deleted or inactivated in respect of (for example) the gene for a virus transcription factor, or the gene IE3, or other mutation mentioned in specification WO 96/04395 (Lynxvale Ltd: PG Speck) such that the herpesvirus has a reduced ability to enter the productive lytic cycle in an infected cell or to cause lysis of an infected cell, in order to reduce or delay herpesvirus toxicity to the infected cells and/or spread in the treated animal. Alternatively the helper-virus can include a temperature-sensitive mutation e.g. corresponding to tsK, with restricted replication competence. The amplicon or a defective helper virus can carry and cause expression of a gene for nerve growth factor (e.g. NGF-beta) to inhibit or delay toxic effects of the amplicon/virus infection. These various measures can be utilised in combination if desired.

However, it is presently considered usually preferable in connection with the present invention not to rely only on mutations or deletions that do not appear by themselves to provide complete abolition of replication-competence, to prevent spread of helper virus after administration of an amplicon preparation to an animal: for example, a deletion of transcription factor may be complemented to some extent by functions present in normal host cells and the gene for transcription factor is therefore not fully essential in the sense used here. Preferably, therefore, any such mutation is accompanied by a deletion in an essential gene of the helper virus, as mentioned above.

Amplicon propagation on the basis of restriction-enzyme-cut helper DNA

In another aspect, the present invention also provides a method of propagating a vector for gene delivery, the vector comprising viral-packaged amplicons that carry at least one gene desired to be delivered to a eukaryotic cell when the amplicon is used as a vector, and the method comprising: providing DNA of a helper-virus that is able to support replication of the amplicon in a host cell; treating the helper-virus DNA with a restriction endonuclease that cuts the helper-virus DNA within one or more non-essential regions to restrict replication of the helper virus while allowing propagation of the amplicon; transfecting or infecting a culture of host cells with a sample of the amplicon (unpackaged or packaged) together with the endonuclease-treated helper-virus DNA, and culturing the host cells thus infected to cause propagation and release of the amplicons in viral-packaged form.

This technique can also help to give an increase in ratio of amplicon to helper-virus in the viral-packaged replication products.

Multiple copies

When a herpesvirus-based amplicon DNA molecule is present in a eukaryotic cell together with a replication-competent herpesvirus, the DNA replication machinery encoded by the replication-competent virus can function to replicate the amplicon molecule by a similar mechanism as that applied to viral DNA replication. A 'rolling-circle' DNA replication process can then lead to long DNA molecules comprising tandem repeated copies of the amplicon DNA, which are cleaved and packaged in units each approximately of the correct size to be packaged into herpesvirus virions. The exact number of repeated units then depends approximately on the length of the starting plasmid and the normal length of the nucleic acid packaged by the selected herpesvirus. For example, HSV has a genome about 150 kb long, and a plasmid/amplicon of unit length about 10 kb can be expected to give rise to packaged amplicons comprising about 15 concatenated copies of the basic amplicon unit with its origin of replication, packaging signal and associated gene(s).

Thus each packaged defective viral (amplicon) genome can contain a multiplicity, e.g. at least 2 or 3, and up to 4, 5, 10, or 20 to 30 copies of the carried foreign gene(s), while most recombinant vectors usually only contain one copy of such foreign gene(s). This can result in a useful increase in the copy number of the genes introduced into cells treated with the amplicons, and increase the extent of expression of the desired gene product(s).

It is an advantage that a packaged amplicon can also take up a comparatively large foreign DNA fragment (e.g. about 10 kilobases (kb) or more, e.g. possibly up to 15 kb, or 20, 30 or 45 kg), which can include several foreign genes to be delivered to the target host cell, e.g. two, three, four or more.

Methods of constructing amplicons

Amplicons can be constructed for example by adaptation of the techniques disclosed in Vlazny and Frenkel, in Proc Nat Acad Sci U.S. 78 (1981) 742–746; and in R. R. Spaete and N. Frenkel, Cell 30 (1982) 295–304; according to the genes desired to be carried.

In connection with the present invention, an amplicon can be constructed which carries several different foreign genes, e.g. up to a plasmid size of about 5, 10, or 15 kb. This can be readily achieved for example by the use of the per-se known cosmid cloning system. The plasmids so constructed (which at some stages of their production form examples of unpackaged amplicons) can then be transfected into a host cell along with a helper virus which is replication-competent in that cell under available culture conditions, and a preparation of the emerging virions then includes packaged amplicons.

Multiple-species amplicon preparations

The invention is not restricted to the preparation and use of a single molecular type of amplicon at any one time. The invention also provides mixtures of amplicons encoding a plurality of e.g. viral antigens, even in certain cases all of the antigens of a given virus. (Alternatively, e.g. in the case of a small virus, it can be desirable to incorporate a number up to all of the viral antigens in a single amplicon.) Amplicons carrying different genes or other nucleic acid can be made separately and mixtures of these amplicons introduced into the packaging cells along with helper virus. The virions emerging from such a packaging cell culture can then include a mixture of different packaged amplicons corresponding to the types introduced.

Such a mixture can contain, for example, antigenic genes of each of a number of different variants of a pathogen, e.g. virus or bacterium. This is especially useful in connection with highly mutable pathogens, such as RNA viruses, for example influenza virus or HIV or SIV or hepatitis C virus, as to which, gene sequences are known, (e.g. in the case of hepatitis C virus from A. M. Delisse et al, in J Hepatol (1991) 13(Suppl 4):520–23; G. Inchauspe et al, (1991) Proc Nat Acad Sci U.S. 88(22):10292–10296; and Q. L. Choo et al, (1991) Proc Nat Acad Sci U.S. 88(6):2451–5).

Thus, for example, a heterogeneous population of virus genomes obtained from a clinical isolate, or from laboratory passage, may be used to provide a starting material for cloning a library of different molecular species by polymerase chain reaction into a single amplicon or set of amplicons used in admixture. This amplicon library is then introduced into the packaging cell along with the helper virus. The virions emerging from the cells include genes derived from a broad range of different genotypes corresponding to the clinical isolate or other heterogeneous source, and can be used as an immunogen or vaccine having a usefully broad range of antigenic diversity.

References herein to genes encoding antigens are understood to include references to genes encoding antigenic fragments of the antigenic proteins occurring in clinical isolates or otherwise in nature, and to fusion proteins incorporating corresponding partial or full aminoacid sequences, and to muteins thereof.

Amplicons as immunogens, vaccines, vaccine adjuvants

Preparations according to the invention can be used as immunogens, for example as vaccines and vaccine adjuvants.

. . . Amplicons encoding antigens

In particular, the present invention provides an amplicon preparation in which the gene or genes carried by the amplicon includes a gene encoding an antigen against which an immune response is desired to be mounted by a mammal such as a human or non-human animal.

Such an antigen-encoding gene can correspond, for example, to a protein (or to an antigenic fragment thereof or antigenically-related fusion protein) from a pathogen such as a virus of the same or a different type than that which is the basis of the amplicon system, for example from a herpesvirus, another type of virus such as an influenza or immunodeficiency virus such as HIV, SIV or FIV, any of a wide range of known bacterial pathogens, eukaryotic parasites such as Chlamydia, or any other infectious agent.

For example, an amplicon based on herpes simplex virus can carry a herpesvirus gene for an antigen such as a HSV viral glycoprotein, e.g. the gD and/or gB protein, which are believed to be the major antigenic targets of immunity to HSV.

Such an amplicon can carry a gene for an antigenic protein of other human and veterinary herpesviruses, such as the gH or other envelope glycoprotein gene of CMV, or the CMV Immediate Early gene, or the gp350 gene of Epstein-Barr virus, or the pseudorabies virus (PRV) glycoprotein gp50.

Also within the scope of the invention are examples in which the immunogenic gene(s) carried by the amplicon for delivery to a treated organism encode: a papillomavirus protein such as L1 or L2; HIV proteins gag, pol, env or nef, or their analogues in other immunodeficiency viruses such as SIV or FIV; SIV gp120 gene; FIV mgENV gene; influenza HA and NP genes; Chlamydia anitgens such as the Chlamydia major outer membrane protein MCMP and Chlamydia heat shock proteins, among many others.

Additionally or alternatively, such an antigen-encoding gene can correspond, for example, to a tumour-associated antigen (or to an antigenic fragment thereof or antigenically-related fusion protein), e.g. any of the known self-coded antigens, such as MAGE-1 and other antigens of the MAGE series identified in T. Boon, Adv Cancer Res 1992, 58, pp 177–210, and/or MZ2-E and other antigens as identified in P. van der Bruggen et al, Science 1991 254 pp 1643–1647; melanoma proteins such as human tyrosinase; mucins such as those identified in P. O. Livingston, Current Opinion in Immunology 1992 4(5) pp 624–629; e.g. MUC1 as identified in J. Burchell et al, Int J Cancer 1989 44 pp 691–696; or any of those tumour-associated antigens known to be encoded by tumour-associated viruses such as human papillomavirus (e.g. E6 or E7 protein of HPV such as HPV type 6, 11, 16 or 18); or Epstein-Barr virus-derived proteins, e.g. those identified in reference 24 and 25 in an article of P. van der Bruggen et al, Current Opinion in Immunology 1992, 4(5) pp 608–612, as well as other tumour associated antigens discussed in that article.

All these carried genes can be represented as sequences coding for partial or complete protein sequences, antigenic fragments or fusion proteins also comprising sequences of other origin.

In this connection, an amplicon can carry for example one or more genes encoding one or more proteins of human papillomavirus such as L1, L2, E6 or E7 proteins, which may for example contain mutations that increase their suitability and safety for vaccine use, as for example the mutations in HPV E7 gene disclosed in specification WO 92/16636 (Cantab Pharmaceuticals: Boursnell et al), which is incorporated herein by reference.

. . . Amplicons encoding immune modulators

In preparations according to the invention, amplicons can for example carry any of a variety of genes with immune modulatory functions, e.g. for cytokines such as interleukins 1 to 15 inclusive, especially for example IL2, IL12, gamma-interferon, tumour necrosis factor, GMCSF, and/or other genes, e.g. those mentioned in specifications WO 88/00971 (CSIRO, Australian National University: Ramshaw et al) and WO 94/16716 (Virogenetics Corp; Paoletti et al).

Also the following genes can be carried by amplicons in connection with the present invention: genes for interferons alpha, beta or gamma; tumour necrosis factor; granulocyte-macrophage colony-stimulating factor (GM-CSF), granulocyte colony-stimulating factor (G-CSF), macrophage colony-stimulating factor (N-CSF), chemokines such as neutrophil activating protein NAP, macrophage chemoattractant and activating factor MCAF, RANTES, macrophage inflammatory peptides MIP-1a and MIP-1b, complement components and their receptors, accessory molecules such as 87.1, 87.2, ICAM-1.2 or 3 or cytokine receptors. Where nucleotide sequences encoding more than one immunomodulating protein are inserted, they may comprise more than one cytokine or may represent a combination of cytokine and accessory molecule(s).

More generally, examples of useful immunomodulating proteins include cytokines, chemokines, complement components, immune system accessory and adhesion molecules and their receptors of human or non-human animal specificity. Useful examples include GM-CSF, IL-2, IL-12, OX40, OX40L (gp34), lymphotactin, CD40, CD40L. Further useful examples include interleukins for example interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1a and MIP-1b, complement components and their receptors, or an accessory molecule such as B7.1, B7.2, ICAM-1, 2 or 3 and cytokine receptors. OX40 and OX40-ligand (gp34) are further useful examples of immunomodulatory proteins. Immunomodulatory proteins can for various purposes be of human or non-human animal specificity and can be represented for present purposes, as the case may be and as may be convenient, by extracellular domains and other fragments with the binding activity of the naturally occurring proteins, and muteins thereof, and their fusion proteins with other polypeptide sequences, e.g. with immunoglobulin heavy chain constant domains. Where nucleotide sequences encoding more than one immunomodulating protein are inserted, they can for example comprise more than one cytokine or a combination of cytokine(s) and accessory/adhesion molecule(s).

The genetic material encoding an immunomodulatory protein can be carried in the vector as an expressible open reading frame encoding a hybrid or fusion protein which comprises a polypeptide region having homology to and functionality of an immunomodulatory protein, linked to a polypeptide region having another homology and optionally another functionality. For example, the immunomodulatory protein can be, comprise, or correspond in functionality to the gp34 protein identified as a binding partner to human Ox-40 (see W. Godfrey et al, J Exp Med 180(2) 1994 pp 757–762, and references cited therein, including S. Miura et al, Mol Cell Biol 11(3) 1991, pp 1313–1325). The version of this protein functionality that can be encoded in the mutant viral genome can correspond to the natural gp34 sequence itself, or to a fragment thereof, or to a hybrid expression product e.g. based on the (C-terminal) extracellular (binding) domain of gp34 fused to another protein, e.g. to the constant region of an immunoglobulin heavy chain such as human IgG1, e.g. with the extracellular domain of gp34 (a type 2 membrane protein) fused at its N-terminal to the C-terminal of the immunoglobulin constant domain.

Others of the immunomodulatory proteins can also be carried and expressed in such derivative and hybrid forms.

It is also understood that mutations of the aminoacid sequences of such immunomodulatory proteins can be incorporated. Included here are proteins having mutated sequences such that they remain homologous, e.g. in sequence, function, and antigenic character, with a protein having the corresponding parent sequence. Such mutations can preferably for example be mutations involving conservative aminoacid changes, e.g. changes between aminoacids of broadly similar molecular properties. For example, interchanges within the alphatic group alanine, valine, leucine and isoleucine can be considered as conservative. Sometimes substitution of glycine for one of these can also be considered conservative. Interchanges within the aliphatic group aspartate and glutamate can also be considered as conservative. Interchanges within the amide group asparagine and glutamine can also be considered as conservative. Interchanges within the hydroxy group serine and threonine can also be considered as conservative. Interchanges within the aromatic group phenylaalanine, tyrosine and tryptophan can also be considered as conservative. Interchanges within the basic group lysine, arginine and histidine can also be considered conservative. Interchanges within the sulphur-containing group methionine and cysteine can also be considered conservative. Sometimes substitution within the group methionine and leucine can also be considered conservative. Preferred conservative substitution groups are aspartate-glutamate; asparagine-glutamine; valine-leucine-isoleucine; alanine-valine; phenylalanine-tyrosine; and lysine-arginine. In other respects, mutated sequences can comprise insertion and/or deletion.

Such preparations can be used as vaccines or vaccine adjuvants. In some embodiments a benefit may be achieved by way of an immune response that contributes to partial protection or amelioration of an underlying condition or susceptibility, e.g. a response that renders it more amenable to other measures by way of therapy or prophylaxis.

Especially for example (but without limitation) in the case of amplicons carrying genes for the immunomodulatory proteins mentioned herein, e.g. cytokines IL2, IL4, IL12, gamma-interferon, tumour necrosis factor, or GMCSF, such preparations can be used in-vitro or ex-vivo to infect live tumour cells and enhance their immunogenicity. Such treated cells can then be used in turn (e.g. after lethal irradiation) as immunogenic material, e.g. in animals carrying the corresponding tumours. This can be achieved for example by an adaptation of the techniques mentioned in G. Dranoff et al, Proc Nat Acad Sci U.S. 90(8) (1993) 3539–3543, or those mentioned in P. Golumbek et al, Immunol Res 12(2) (1993) 183–192, or in P. Golumbek et al, Science 254 (5032) (1991) pp 713–716.

Amplicon preparations according to embodiments of the invention, e.g. those encoding tumour antigens or immune regulatory molecules, can be used in cancer immunotherapy, either directly by administration to a patient, e.g. systemically or by direct injection into a tumour, or alternatively by ex-vivo procedures involving priming and/or stimulation of immune system cells from a patient to be treated, by means of the amplicon preparations and/or cells infected therewith.

In view of the possible risks associated with uses of replication-competent recombinant viruses that carry genes for the modulation of host immune responses, it is strongly preferred in connection with the present invention that such modulatory genes are carried by amplicons used in association with replication-defective viruses lacking a gene essential for the production of infectious new virus particles, as described above, so that even if a recombination were to arise between the amplicon and the helper virus, the resulting virus would be prevented from spreading from treated to untreated host animals.

Amplicons based on a range of virus types

Amplicons can be made on the basis of a variety of virus types. They can for example be made on the basis of herpes simplex virus as described below and/or as described by R. R. Spaete and N. Frenkel, Cell 30 (1982) 295–304. Amplicons can also be made for example on the basis of other herpesvirus such as Marek's disease virus (MDV), using a DNA encoding an origin of replication characteristic of MDV or other virus as described or cited by Camp et al, in J Virol 65(11) (1991) 6320–6324; or in U.S. Pat. No. 4,995,152 (Carter et al); or other literature of amplicons as mentioned therein. Plasmids for use as amplicons can be constructed for example on the basis of the per-se known cosmid cloning system, especially advantageous where the size of the genetic material to be carried by the amplicon is of the order of 5–10 or more. The insertion of desired genes into amplicons can be carried out on the basis of rDNA techniques known per-se, on the basis of genes obtained and cloned from DNA prepared from any of a variety of wild-type source organisms, using PCR or other per-se known technique.

Production and use of amplicon-containing preparations

Preparations according to the invention can be made and formulated with known carriers, excipients, preservatives and adjuvants, especially those known and used or proposed for use in connection with live virus vaccines, at choice, under normal good pharmaceutical manufacturing practice, so that they can be suitable, in connection with certain embodiments of the invention, for parenteral administration to human and non-human animal subjects or for the treatment of live cells that will be introduced or reintroduced into such a subject.

They can be introduced into a whole animal organism by any of the routes known for administration of vaccines and virus vectors, for example subcutaneous, delivery to a mucosal surface such as oral, nasal, or vaginal mucosa, or by direct injection into a tumour.

Dosages can range from for example 10^2 to 10^8 pfu, e.g. from 10^4 to 10^8 pfu.

They can be administered to an animal which has no current disease or to an animal which has (or has had) a disease, either in a period of active disease and/or presence of lesions, or in a period of remission or latency.

Preparations according to the invention can also be introduced into animal cells ex-vivo or in-vitro, e.g. for the purpose of infecting the cells and making derivative cell preparations that carry the DNA desired to be introduced into such cells, e.g. for later introduction of such treated or derivative cells into an animal host, or for in-vitro diagnostic purposes.

Amplicon preparations according to examples of the invention can be used as immunogens, for prophylactic or therapeutic use, direct or indirect, in generating an immune response in a subject treated therewith. The immune response can be against a heterologous antigen encoded by the amplicon. The amplicons can also be used in the preparation of an immunogen such as a vaccine for therapeutic or prophylactic use in tumour therapy. For example examples of the preparations can be used in the in-vitro priming, stimulation or expansion of (e.g. virus-specific) cytotoxic T cells.

Thus amplicons or amplicon-treated cells such as for example tumour cells treated by the techniques mentioned above) can be used ex-vivo (in-vitro) to stimulate and/or prime cytotoxic lymphocytes, e.g. deriving from a patient; such primed CTLs can then be reinfused into a patient or other subject to be treated to confer a degree of immune response against either cell-related or amplicon-related antigens.

Examples of amplicon vector preparations according to this invention can be used in processes of providing an immunostimulus to a treated human or non-human animal subject, e.g. for purposes of cancer immunotherapy. The use of the vectors can be either direct, e.g. by administration to the subject, e.g. into the site of a solid tumour, or it can be indirect, for example the use of the vector can comprise:

(i) contacting the vector preparation ex-vivo with a preparation of cells capable after infection with the vector of providing an immunostimulus to a subject to be treated; and (ii) using the infected cells to deliver an immune stimulus to the subject to be treated, e.g.

(a) by direct administration of the infected cells as a vaccine e.g. after inactivation before administration, e.g. after irradiation, or (b) by indirect use of the cells to prime or stimulate ex-vivo immune-competent cells such as cells of the immune system of the subject to be treated, followed by re-administration of the immune-competent cells e.g. without concurrent administration of virus or virus-infected cells. Any cells unwanted in this connection can for example be removed by a purification process comprising negative depletion, e.g. by selective removal of cells of unwanted type e.g. with corresponding antibodies or other binding agents.

Cells infected ex-vivo with the vector can be either autologous cells or heterologous cells, e.g. heterologous cells obtained from one or a plurality of subjects with a condition similar to that which is to be treated. The cells can be of a single cell type or of a mixture of cell types, e.g. they can comprise cells of one or plural cell lines established from clinical tumour samples. Thus, for example, in the case where an immune stimulus is to be given, directed against melanoma cells, the heterologous cells can be melanoma cells from one or more subjects with melanoma, other than the subject to be treated, or including the subject to be treated. Corresponding arrangements can be made for other specificities of immune stimulus.

The infected cells for administration to provide an immune stimulus can preferably be inactivated, e.g. by irradiation, before administration. They can preferably be incubated for a sufficient time before inactivation to allow them to express the heterologous gene carried by the viral vector.

The infected cells can be used to deliver an immune stimulus to the subject to be treated by use of the cells to prime or stimulate ex-vivo immune-competent cells such as cells of the immune system of the subject to be treated, followed by re-administration of the immuno, competent cells e.g. without concurrent administration of amplicon or cells infected therewith.

The cells infected ex-vivo with the amplicon preparation can be autologous cells, or heterologous cells, e.g. comprising cells of a tumour cell line such as a melanoma cell line.

According to examples of the invention there is also provided a dosed or calibrated preparation of vector-infected, optionally inactivated cells, for administration to a subject to be treated to an immune stimulus, which has been dosage-calibrated, e.g. by reference to the number or concentration of infected cells it contains, or by reference to the quantity of heterologous gene product it expresses.

Alternatively the genetically disabled virus vectors can be used in in-vivo administration of a quantity or concentration of the virus vector to contact and thereby infect tumour cells in vivo, e.g. cells of a solid tumour such as for example a melanoma.

Among the cells that can usefully be treated in this way are for example malignant cells of human and non-human animals, especially for example malignant cells related to blood cells, e.g. leukaemic cells, e.g. CO34+ cells (haematopoietic cells) (see, for example, cell types as mentioned in R. Jurecic et al, ch 2, pp 7–30 in 'Somatic Gene Therapy' CRC Press 1995, ed. P. L. Chang).

Immunological treatment of tumours using cytokines is reviewed by H. Tahara et al, ch.15, pp 263–285 in 'Somatic Gene Therapy' CRC Press 1995, ed. P. L. Chang). The vectors described herein can be applied to the immunological applications of the cytokines and methods of treatment reviewed in the cited review by H. Tahara et al, using appropriate adaptations and modifications as will be readily apparent to those skilled in the field.

The invention also finds further application in vitro for example in in vitro treatments such as expansion of T cells such as virus-specific cytotoxic T cells. Two complications of many immunosuppressive or cytotoxic treatments are generalised viraemia following virus infections and expansion of virus-transformed cells as a result of latent virus reactivation. This is due to the fact that the normal mechanism for controlling such infections is impaired as a result of the treatment. One possible solution to this problem is to produce in vitro the appropriate cytotoxic T cells which are capable of controlling the virus infected cells. This can be done by isolating peripheral blood mononuclear cells or lymphocytes or T cells prior to treatment of the patient and stimulating such cells in vitro with a preparation of live virus. It is necessary to use live virus as cytotoxic T cells are generally directed against peptides derived from foreign proteins which are synthesised within the antigen-presenting cell; inactivated virus or individual proteins are very poor at raising cytotoxic T cell responses. The activated cells are then expanded in culture over a period of weeks with further re-stimulation with antigen and a growth factor such as interleukin-2. However, there is the concern that there might be residual live virus in the cull cultures when the CTLs are re-infused into the patient. Use of a disabled virus capable of inducing CTL activity but incapable of spread within the patient, if inadvertently given along with the in vitro expanded cells, can therefore provide an advantage over a system that uses replication competent virus.

Hence the invention further provides a method for producing virus-specific cytotoxic T cells which method comprises:

(a) isolating a sample of blood mononuclear cells, lymphocytes or T cells from a patient;

(b) culturing said sample in vitro in the presence of an amplicon preparation according to an example of the present invention and which can optionally include a heterologous nucleotide sequence which encodes an immunomodulating protein; and (c) reinfusing cultured cells into the patient.

Certain vectors provided by the present invention can be applied to gene therapy, e.g. corrective gene therapy. In such an application the vector can encode a gene to be delivered by way of corrective gene therapy, e.g. a gene encoding ADA or another gene to be administered for such a purpose e.g. as mentioned above. A vector as described herein encoding the immunomodulatory protein TGF beta can be particularly suitable as a vector for corrective gene therapy, to downregulate the response of the treated subject, who will usually be treated either directly with a vector provided hereby or with live cells, autologous or heterologous, after their infection with the vector.

Negative immunomodulatory effects can be provided by suitable choice of immunomodulatory proteins. Further choice of immunomodulatory proteins for this application can for example be as follows: Inhibition of Th1 effects can be achieved with vectors encoding Th2 cytokines or vice versa: for example a vector encoding IL10 against Th1 effects and a vector encoding IFN-gamma against Th2 effects. Immune response can be further downregulated by using a vector that encodes for example an immune downregulating gene of viral or other pathogenic origin, e.g. a vector encoding a herpes ICP47 gene (from HSV1 or HSV2) or additionally encoding another known immune-downregulating gene, e.g. E3-gp19k of adenovirus (see G. Fejer et al. J Virol 68 (1994) 5871–81)).

Literature procedures of gene therapy, e.g. U.S. Pat. No. 5,399,346 (W. F. Anderson et al), can be adapted with the use of the vectors provided hereby.

The invention is further illustrated by the following example preparations which give indications relating to the production of HSV-based amplicons which (with any necessary routine adaptation of the techniques) can be made carrying genes for SIV gag-pol, Nef, or HPV E6/E7 (or GM-CSF and/or B7.1) and which are able to propagate with the help of a gH-defective herpes simplex virus and a complementing recombinant cell line that expresses HSV gel.

DETAILED DESCRIPTION OF EXAMPLE PREPARATIONS

The description below gives indications for the construction of amplicons based on herpes simplex virus (HSV) and containing functional copies of the genes encoding the immunoregulatory proteins murine GM-CSF, murine B7.1 and certain antigens derived from the pathogens human papillomavirus (HPV) or simian immunodeficiency virus (SIV). These amplicons can then be used in conjunction with a genetically-disable helper-virus system, for delivery of these foreign genes to host cells either in vitro or in vivo. The methods may however readily be applied and adapted to the delivery of any gene or combination of genes using the same amplicon/helper-virus system, or any other equivalent amplicon/helper-virus system, e.g. from other herpesviruses.

The individual molecular biological techniques used are per-se known, e.g. those essentially as set out in 'Molecular Cloning, A Laboratory Manual' eds Sambrook, Fritsch and Maniatis, Cold Spring Harbor Laboratory Press, 1989 or other edition.

In the following description the expression 'defective virus' is often used to denote virally-packaged amplicons. Construction of basic amplicon plasmids based on HSV-1

Initially a basic amplicon is constructed. This basic amplicon, called pW7, is used to construct all the other examples of amplicons mentioned below, containing different foreign genes. The following section describes the detailed procedures of their construction.

Amplicon pW7

Amplicon pW7 can be constructed using plasmid vector pAT153 (Stow et al, Nucleic Acid Res 11 (1983) 8205–8220; Cancer Cells 4/DNA Tumour Viruses (1986) 497–507). Initially a 535-bp Sau3A fragment which specifies a functional origin of HSV-1 DNA replication (ORIs) is inserted into the BamHI site of pAT153. Then a HinfI joint fragment of HSV-1, which has been completely sequenced and contains a packaging signal in a single 'a' sequence of HSV-1 genome, is inserted into the Hind III/EcoRI site. pW7 can be replicated and packaged in suitable mammalian cells in the presence of helper HSV viruses, owing to the insertion of these two crucial HSV-1 components.

pW7lacZ pW7lacZ is a modified version of basic amplicon pW7. It is constructed by inserting a gene cassette composed of bacterium lacZ gene driven by a HSV IE110 promoter and tailed by SV40 polyA signal, into the unique EcoRV site of pW7. The blue x-gal staining from lacZ gene expression is useful for detecting the ratio of defective and helper viruses in vitro and the efficacy of gene delivery into cells in vivo.

pW7TK+ pW7TK+ is another modified version of basic amplicon pW7. It is constructed by inserting a copy of HSV TK gene into the unique EcoRV site of pW7. When a TK-negative mutant HSV is used as helper virus, methotrexate can be used in the propagation medium select in favour of defective virus, as described above.

Cloning of heterologous genes into the HSV amplicon

Amplicon vectors for foreign gene expression are constructed as follows. Initially a plasmid is constructed that contains a strong eukaryotic promoter adjacent to a useful set of cloning sites. This plasmid, termed pMX1.1, is constructed as follows:

pIMX1.1

Construction of this plasmid uses plasmid pIMMB63, which is made from HSV-1 strain KOS(m) DNA. pIMMB63 contains sequences flanking the HSV-1 gH gene, with a central unique HpaI site. Any gene cloned into this site can therefore be inserted by recombination into the HSV-1 genome at the gH locus. (If the virus is a TK-negative virus lacking the 3' end of the TK gene then the plasmid will replace the 3' end of the TK gene and restore TK activity, allowing selection for TK+ virus.)

Plasmid pIMMB63 is made as follows. Two PCR fragments are made by pairs of oligonucleotides MB98-MB63, and MB61-MB58, respectively, on the basis of HSV-1 KOS(m) DNA.

The oligonucleotides used are as follows:

```
              HindIII
MB98    5' TCAAAGCTTATGGCTTCGTACCCCTGCCAT 3'    (SEQ ID NO:1)
              ......

HpaI
MB63    5' TCAGTTAACGGACCCCGTCCCTAACCCACG 3'    (SEQ ID NO:2)
              ......

HpaI
MB61    5' TCAGTTAACAGCCCCTCTTTGCTTTCCCTC 3'    (SEQ ID NO:3)
              ......

EcoRI
MB58    5' TCAGAATTCGAGCAGCTCCTCATGTTCGAC 3'    (SEQ IS NO:4)
```

The resulting PCR fragments are digested with restriction enzymes appropriate to the restriction sites included in the oligonucleotides. The MB98-MB63 fragment is digested with HindIII and HpaI. The MB61-MB58 fragment is digested with HpaI and EcoRI. These fragments are then ligated into the vector pUC119 (J. Vieira and J. Messing, Methods in Enzymology 153 (1987) 3–11) which has been digested with HindIII and EcoRI. The resultant plasmid is PIMMB63.

Then the plasmid pRC/CMV (Invitrogen Corporation) is digested with NruI and PvuII, and a 1066 bp fragment, which contains the CMV IE promoter and a polyA signal, is blunt ended and inserted into the unique HpaI site of plasmid pIMMB63.

The resulting plasmid is named pIMX1.1, and contains a unique site for digestion by the restriction enzyme BsaBI, which is useful for the insertion of heterologous DNA adjacent to the CMV promoter.

A second useful plasmid, to allow simultaneous expression of two different genes from the amplicon, is constructed by introducing a second promoter, derived from the Rous Sarcoma virus (RSV) long terminal repeat sequence (LTR), adjacent to the CMV promoter in pMX1.1, but oriented so that expression of a gene from this promoter is driven in the opposite direction from that of the CMV promoter. This plasmid is termed pMX6.0, and is constructed as follows:

pIMX6.0

Plasmid pREP-4 (from Invitrogen Corporation) is digested with SalI and the 1012 1084 bp DNA fragment containing RSV LTR and SV40 poly A signal cassette is isolated and treated to remove the 3' single stranded DNA overhang created by restriction enzyme digestion, to leave it blunt-ended. This DNA fragment is then cloned into the Hinc II restriction site of pIMX1.1, The resulting plasmid pIMX6.0 contains a unique SfiI restriction site between the RSV LTR promoter and the SV40 polyadeylation signal (poly-A) which can be used for the cloning and expression of inserted, e.g. heterologous, genes.

Amplicon vectors for expression of the immunomodulatory genes GM-CSF and B7.1 can be constructed as follows:

pIMX4.0

Plasmid pIMX4.0 is a recombination vector which contains a copy of the gene encoding murine GM-CSF placed under the control of a CMV IE promoter. This plasmid is constructed by inserting a copy of the murine GM-CSF gene, which has been excised from plasmid gPM3.2FF (Gough et al, EMBO J 4 (1985) 645–653) with restriction enzymes SmaI and DraI, into the unique BsaBI site of pIMX1.1.

pIMX7.0

This plasmid is a another recombination vector which is constructed based on pIMX6.0 and it too contains murine GM-CSF driven by a CMV IE promoter. This plasmid is constructed by inserting a further sample of the same isolated DNA fragment containing the murine GM-CSF gene as excised from plasmid pGM3.2FF (Gough et al, EMBO Journal 4 (1985) 645–653) with SmaI and DraI, into the unique BsaBI site of pIMX6.0.

pIMX8.0

This plasmid is constructed on the basis of pIMX7.0 and contains both murine GM-CSF and B7.1 genes, placed under the control of the CMV IE promoter and RSV LTR, respectively. Construction is achieved by inserting a copy of the gene encoding murine B7.1, as excised from plasmid piLN-murB7 with restriction enzymes Hind III and XbaI, into the unique SfiI site of pIMX7.0.

Finally, a fragment of DNA comprising both the GM-CSF and B7.1 genes under the control of the CMV and RSV LTR promoters respectively is inserted into the basic amplicon plasmid pW7 to create the amplicon expression vector pAMP1.0.

pAMP1.0

This amplicon, containing both murine GM-CSF and B7.1 genes, is constructed by isolating the DNA fragment containing these two genes, as excised from pIMX8.0 with restriction enzyme SmaI, and cloning it into the unique EcoRV site of pW7.

Construction of amplicon vector for expression of antigenic sequences from SIV

By using similar strategies adapted from the construction of pAMP1.0, amplicons containing SIV gag-pol and Nef genes may also be constructed. Plasmid MV12, which was originally constructed by cloning the gag-pol region (nucleotides 1048–5760) from SIVmac 251 (32H isolate, clone pJ5) into EcoRI site of plasmid MV11, is digested with EcoRI and a 4712 bp fragment containing gag-pol is cloned into the unique BsaBI site of pIMX6.0. Then SIV Nef gene is inserted into the unique SfiI site of the same plasmid. So the resultant plasmid will contain SIV gag-pol gene driven by CMV IE promoter and Nef gene driven by RSV LTR. The cassette containing these two genes is then excised out with SmaI and cloned into either pW7 or pW7TK+.

Construction of an amplicon vector for expression of a "SIV gene library"

An amplicon containing a CMV promoter is constructed by cloning a CMV IE promoter and a BGH polyA cassette from pRC/CMV (see above) into the single HindIII site of pW7 or pW7TK+. (This is done by blunt-end ligation, thus destroying the unique HindIII site.) SIV genes such as gag-pol and Nef are amplified by polymerase chain reaction (PCR) from a pool of blood samples of a variety of patients, by using primers which leave a NotI site at one end and a XbaI site at the other end of the amplified SIV gene fragments. Accordingly, the amplicon containing a CMV promoter is digested with both NotI and XbaI and gel purified (both of these restriction enzymes make a cut at a unique position at the multiple cloning site between the CMV promoter and the terminal signal of the amplicon). The terminal ends generated by these two enzymes are not compatible, thus preventing self religation. The PCR products are then cloned into the amplicon through orientated cohesive-end ligation. A stock of defective virus can be made from these amplicons and this stock should contain gag-pol and Nef gene sequences from many SIV variants.

The technique can readily be adapted to the construction of amplicons containing genes from HIV as well as SIV in many variants. Frequent genetic mutation which results in antigenic variation has been thought to cause evasion by HIV of host's immune surveillance. This has been considered a major obstacle for HIV vaccine development. The present technique of making a stock of defective HSV virus amplicons carrying a wide range of SIV or HIV variant genes provides material for generating a useful immunogenic or vaccine response to such antigens and their variants.

Construction of amplicons containing HPV genes

By using similar strategies adapted from those already mentioned above, amplicons containing HPV E6/E7 genes, may also be constructed. The genes from HPV can for example be from the sources and can include the mutations described in specification WO 92/16636 (Cantab Pharmaceuticals: Boursnell et al).

Construction of type I HSV gH deletion mutant as a helper virus for preparation of defective virus (packaged amplicon) stocks In order to obtain a safe helper virus for preparation of defective virus for vaccine development purpose, a type I gH deletion mutant is generated. A gH deletion mutant of HSV is a genetically disabled virus that can be propagated only on a complementing cell line that expresses viral gH, see specification WO 92/05263 (Immunology Ltd: Inglis et al). HSV gH gene encodes the essential glycoprotein H (gH) which is required for virus infectivity (see also Forrester et al, J Virol 66, 341–348, 1992). In the absence of gH protein expression, the gH-negative HSV can provide almost the complete repertoire of viral proteins which fulfil the requirement as a helper virus for defective virus preparation. When the gH-negative HSV, however, infects host cells that are not complementing in relation to the viral gH, virus-like progeny particles are formed but they are not able to infect other host cells, and thus spread of the virus by infective virus particles within the host, and spread to untreated hosts, is prevented.

Construction of a type I gH expression cell line

Such a cell line is used to generate and grow up gH deletion mutant virus. One example of such a cell line is described in specification WO 92/05263.

An alternative method of construction of such a cell line is as follows. A plasmid pIMC05 is used. Plasmid pIMC05 can be constructed as follows: A 4.3 kb Sst-I fragment encoding the HSV-1 (HFEM) gH gene and upstream HSV-1 gO promoter (−392 to +11) is excised from the plasmid pgDBrgH (see Forrester et al., J. Virol. 66, 341–348, 1992) and cloned into vector pUC119 (J Vieira and J Messing, Methods in Enzymology 153 (1987) 3–11) to produce plasmid pUC119gH. A NotI site is introduced into plasmid pUC119gH by site-directed mutanenesis, 87 bp downstream of the stop codon. The resulting plasmid, pIMC03, is used to generate a NotI-SstI fragment which is repaired and ligated into the eukaryotic expression vector pRC/CMV (Invitrogen Corporation), pre-digested with NotI and NruI to remove the CMV IE promoter. The resulting plasmid can be designated pIMC05 and contains the HSV-1 gH gene under the transcriptional control of the virus indicuble gD promoter and BGH (bovine growth hormone) poly A. It also contains the neomycin resistance gene for selection of G418 resistant stable cell lines.

Plasmid pIMC05 can then be transfected into Vero cells (ATCC no. 88020401) using the calcium phosphate technique (Sambrook, Fritsch & Maniatis, A Laboratory Manual, Cold Spring Harbor Laboratory Press). Cells are selected by dilution cloning in the presence of G418 and a clonal cell line is isolated. Following expansion and freezing, cells are seeded into 24 well plates and tested for their ability to support the growth of gH-negative virus, by infection with SC16-del-gH (see Forrester et al., J. Virol. 66, 341–348, 1992) at 0.1 pfu/cell. Virus plaques can be observed 3 days post-infection, confirming expression of the gH gene.

Construction of plasmids used for generation of type I gH deletion mutant pIMMB25

Flanking sequences to either side of the gH gene are amplified from HSV-1 strain KOS(m) viral DNA by the polymerase chain reaction (PCR) using Vent DNA polymerase (New England Biolabs) which has a lower error rate than Taq DNA polymerase. The fragment amplified with oligonucleotides MB62 (TCAAAGCTTCTGCAGGGCGGCGGGTCGTGG) (SEQ ID NO:5) and MB63

(TCAGTTAACGGACCCCGTCCCTAACCCACG) (SEQ ID NO:6) is digested with EcoRI and HpaI, and the fragment amplified with oligonucleotides MB61-MB58 (same as the ones used to construct pIMMB63 described herein) is digested with HpaI and HindIII. These fragments are gel-purified and cloned into EcoRI-HindIII-cut pUC119. The resultant plasmid is designated pIMMB25.

pIMMB27+

A CMV-lacZ cassette is excised from the vector pMV10 (Forrester et al, J Virol 66 (1992) 341–348) by digestion with HindIII. The fragment is made blunt-ended by repair with Klenow polymerase and then gel-purified. The purified fragment is cloned into the HpaI site of pIMMB25. A clone in which the CMV-lacZ cassette is inserted in the same orientation as the gH gene is selected. This plasmid is designated pIMMB27+.

Generation of gH deletion mutant

Recombinant virus is constructed by transfection of type I HSV (strain sc16) viral DNA with the plasmid pIMMB27. Viral DNA is purified on a sodium iodide gradient as described in Walboomers & Ter Schegget (1976, Virology 74, 256–258). Recombination is carried out as follows: A transfection mix is prepared by mixing 5 micro-g of viral DNA, 0.5 micro-g of linearised plasmid DNA (linerised by digestion with the restriction enzyme ScaI) in 1 ml of HEBS buffer (137 mM NaCl, 5 mM KCl, 0.7 mM Na\2HP04, 5.5 mM glucose, 20 mM Hepes, pH 7.05). 70 micro-l of 2M CaCl\2 is added dropwise, and mixed gently. The medium is removed from a sub-confluent 5 cm dish of completing cells expressing type I gH and 500 micro-l of the transfection mix is added to each of two dishes. The cells are incubated at 37 deg.C. for 40 minutes, when 4 ml of growth medium containing 5% foetal calf serum (FCS) are added, 4 hours after adding the transfection mix, the medium is removed and the cells washed with serum-free medium. The cells are then 'shocked' with 500 micro-l per dish of 15% glycerol for 2 minutes. The glycerol is removed, the cells washed twice with serum-free medium and growth medium containing 5% FCS is added.

After 4–7 days, when a full viral cytopathic effect (CPE) is observed, the cells are scraped into the medium, spun down at 2500 rpm for 5 minutes at 4 deg C., and resuspended in 120 micro-l of Eagles minimal essential medium (EMEM). This is now a crude virus stock containing wild-type and recombinant virus. The stock is frozen, thawed and sonicated and screened for recombinants on complementing cells expressing type I gH at a range of dilutions. After addition of the virus dilutions, the cells are overlaid with medium containing 1% low-gelling temperature agarose. After the appearance of viral plaques at about 3 days, a second overlay of agarose containing 330 micro-g/ml of Xgal is added. Blue plaques are picked, within 48 hours, and transferred to 24-well dishes (1 sq cm per well) containing complementing cells expressing type I gH. The plaques are allowed to grow to full CPE and harvested by scraping into the medium. Multiple rounds of plaque-purification are carried out until a pure stock of virus is obtained.

The structure of the recombinant is confirmed as follows. Sodium iodide purified viral DNA is prepared as before, and digested with BamHI. This digest is separated on an agarose gel and transferred to a nylon membrane. This is probed with a radiolabelled DNA fragment homologous to the sequences either side of the gH gene.

Generation of defective virus stocks containing foreign genes

The DNA of foreign gene-containing amplicons is co-transfected with purified genomic DNA of the gH-negative HSV-1 (or other example of genetically-disabled herpesvirus) into complementing cells expressing the appropriate gene product, in this case type I gH, by the transfection procedure mentioned above. Virus preparations are made by harvesting these co-transfected cells at various times after initial DNA transfection. A larger viral stock can be made by simply using these virus preparations to infected some more complementing cells expressing type I gH. The ratio of defective virus to helper virus is checked by Southern hybridisations on the DNA extracted from these viral preparations. If necessary, this ratio can be adjusted by varying the amounts of amplicon and helper virus DNA used for transfection, or the infection time, as it has been reported that defective virus may be preferentially assembled at a late stage of infection.

In order to achieve a higher percentage of defective virus in the viral stock, two novel strategies can be employed according to the present invention:

1) In order to achieve a higher ratio of defective over helper virus in the stock preparation, a HSV amplicon containing HSV thymidine kinase gene, pW7TK+, is used to carry foreign gene(s), and TK-minus gH– HSV is used as helper virus: the propagation is carried out on a gH+ complementing recombinant cell line. In the presence of methotrexate in the growth medium, virus can only grow in those cells which are infected by both defective and helper viruses. This procedure will selectively amplify the defective virus and increase its ratio over helper virus in the stock.

2) Alternatively, purified HSV DNA is initially digested with restriction enzymes which only cut type I HSV DNA once or twice (such as SpeI and/or AseI). Once the enzyme-digested viral DNA is co-transfected with amplicon DNA into suitable cells, it provides all the helper functions, as does undigested HSV DNA, but it has reduced capacity to generate new helper virus particles.

This technique is illustrated by the following comparison experiment, using amplicon PW7 lacZ1 (the IE110 promoter driving the lacZ gene cloned into the PW7 amplicon described above). (In this example, the lacZ gene encodes a 'reporter' enzyme lacZ, which is employed here for experimental purposes of demonstration. In the practice of the invention corresponding to this experimental example, the place of the lacZ gene in this example will generally be taken, or supplemented, using readily available rDNA techniques, by one or more other genes along with their promoters, encoding antigens or other products of interest in connection with the application of the invention, e.g. as mentioned elsewhere herein).

In order to propagate amplicons with cut DNA, a preparation of high- molecular-weight infective DNA of HSV-1 strain SC16 is digested with restriction enzyme AseI. This cuts the genome twice at positions 1593 and 124777 but does not disrupt any currently identified gene product. Such digestion does however abolish or reduce the ability of the viral DNA to give rise to infectious progeny virions.

Vero cells were transfected with amplicon PW7 lacZ1 (3 micro-g) and with the AseI-cut SC16 DNA (10 micro-g). After transfection, the cells were cultured for 3 days, then viral progeny was harvested and assayed (after infection of a further assay culture of Vero cells) in the presence of standard substrate X-gal, which generates a blue product with lacZ enzyme.

Blue cells in the assay represented cells infected by the lacZ-carrying amplicon, and white plaques in the assay indicated cells infected by helper virus. Under the chosen culture conditions, the harvest assayed at $1.8 \times 10^4$ pfu/ml amplicon titre and $3 \times 10^3$ helper virus titre (ratio of helper to amplicon of 1.:6).

Under corresponding conditions for comparison, without the use of the restriction enzyme, the titres obtained were 1.3×10^4 pfu/ml amplicon and 1.5×10^5 pfu/ml helper virus. It emerged that the use of the restriction enzyme before the propagation depressed the output of helper virus by nearly two orders of magnitude, and enriched the content of amplicon relatively to helper virus in the harvested virion progeny particles, by a factor of 78.

Test of expression of foreign genes contained in the defective viruses

The expression of the foreign genes in the defective viruses can either be tested by SDS-PAGE gel analysis (in the case of SIV genes and HPV E6/E7), or by functional assay (in the case of GM-CSF and B7.1).

For SDS-PAGE analysis, complementing cells expressing type I gH can be infected with defective virus stocks and labelled with 35-S methionine. Twenty-four hours after infection, total proteins are extracted and are subjected to immunoprecipitation with anti-SIV gag-pol, Nef, or anti HPV E6/E7 proteins. Antibody precipitated proteins can be subjected to SDS-PAGE separation and auto-radiography.

Functional assay for GM-CSF can be carried out by bioassay of supernatant from culture of a host cell line infected with helper virus and amplicons carrying GM-CSF genes, in known manner using any known CMCSF responsive cell line.

Test of vaccine potential of amplicons (defective viruses) containing foreign genes Suitability of amplicons (defective virus) containing GM-CSF and/or B7.1 as vaccine adjuvant The suitability of any given specimen of amplicons (defective viruses) containing immune modulators such as GM-CSF and B7.1 as a adjuvant can be assessed by its effect on enhancing HSV vaccine potency which can be tested in a mouse model as described in Farrell et al., J. Virol. 68, 927–32, 1994, by comparing the HSV-specific immunity given by gH-negative HSV-1 alone and the immunity given by a mixture of amplicon (defective virus) and gH-negative HSV-1 together. Groups of mice are vaccinated by scarification of the ear pinna with varying doses (ranging from 10^2 to 10^6 pfu) of the viruses. A control group is vaccinated with PBS. Three weeks post vaccination mice are challenged in the opposite ear pinna with 10^6 pfu of wild-type HSV-1 (strain SC16). Five days post challenge the mice are killed and the challenged ears removed and frozen at −70 deg C. The ears are homogenised and the amount of infectious challenge virus in each ear is determined by plaque titration. The reduction in virus titres in the vaccinated groups of mice compared to the PBS-treated controls is a measure of the protection afforded by the virus vaccine.

It is known that the gH-related virus can completely abolish the presence of infectious virus at a vaccinating dose of 5×10^5 pfu, whilst even at 5×10^4 pfu a reduction of 3 logs is observed.

The virus stock which contains defective virus containing GH-CSF and/or B7.1 is likely to increase this level of protection: complete protection from any infectious virus might be observed at lower challenge doses than in the gH-deleted virus vaccinated mice, and a greater reduction of infectious virus titres might be found compared to the PBS-vaccinated controls.

Efficacy of amplicon gene delivery for vaccine development

The efficacy of gene delivery by defective HSV virus can be assessed through two stages. At stage 1, defective viruses containing SIV and HPV genes are used to vaccinate mice and CTL assays are carried out to assess their ability to generate corresponding cell-mediated immune response. For defective viral samples for which the result is encouraging, a stage 2 test can suitably be carried out. Animal models can be set up and these recombinant defective viruses can be tested for their beneficial effect on tumours expressing E6/E7 genes or their ability to prevent or ameliorate challenge of monkeys with wild type SIV. Other tests of effect of these and other constructs will be readily accessible to those skilled in the art.

The invention described herein is susceptible to modifications and variations that will be apparent to the reader of ordinary skill in the field, and the above disclosure methods also to combinations and subcombinations of the features mentioned or described herein and in the cited publications, which are hereby incorporated by reference in their entirety.

We claim:

1. A preparation of a herpesvirus amplicon comprising an origin of replication, a packaging sequence, and at least one inserted gene encoding an antigen or an immunomodulatory protein under control of a promoter, in association with helper herpesvirus of DNA thereof, wherein the associated helper virus has an inactivating defect in respect of a gene that is essential for the production of infectious new virus particles, such that the helper virus cannot cause production of infectious new virus particles except when said virus infects recombinant complementing host cells which have been made to carry and can express a gene that provides the function of said essential viral gene.

2. The preparation according to claim 1, wherein the essential viral gene is an essential viral glycoprotein, e.g. gH, gD, gB or gL or a homologue thereof.

3. The preparation according to claim 1, wherein said inserted gene encodes an immunomodulatory protein selected from cytokines, chemokines; and immune system accessory molecules and adhesion molecules and their receptors.

4. The amplicon preparation according to claim 1 wherein the amplicon encodes a gene for a function needed for helper virus replication, so that said preparation can be propagated in a host cell culture under conditions where the amplicon is essential to propagation of the helper virus.

5. The preparation according to claim 1, wherein the helper virus is in the form of DNA that has been cut with restriction endonuclease in a nonessential site, to restrict replication of the helper virus.

6. A method of in-vitro expansion of cytotoxic T cells, which comprises contacting T-cells to be used for said expansion with an amplicon preparation according to claim 1, whereby said cytotoxic T-cells are expanded.

7. The preparation according to claim 1, wherein said inserted gene encodes a heterologous antigen.

8. The preparation according to claim 7, wherein said heterologous antigen comprises a tumor-associated antigen.

9. The preparation according to claim 7, wherein said heterologous antigen comprises a viral antigen.

10. The preparation according to claim 9, wherein said amplicon preparation comprises a mixture of amplicons encoding a plurality of viral antigens, e.g. multiple antigens from a virus heterologous to the amplicon, e.g. Influenza virus or HIV or SIV or a hepatitis C virus.

11. A pharmaceutical preparation comprising a preparation according to claim 1.

12. The pharmaceutical preparation according to claim 11, for use as an immunogen, such as a vaccine or vaccine adjuvant.

13. A preparation of a herpesvirus amplicon comprising an origin of replication, a packaging sequence, and at least one inserted gene under control of a promoter, in association with a helper virus or DNA thereof, wherein the associated helper virus has an inactivating defect in respect of a gene that is essential for the production of infectious new virus particles, such that the helper virus cannot cause production of infectious new virus particles except when said helper virus infects recombinant complementing host cells which have been made to carry and can express a gene that provides the function of said essential viral gene; and wherein the amplicon carries an inserted gene necessary for the propagation of the helper virus.

14. The preparation according to claim 13, wherein the amplicon carries an inserted TK gene, the helper virus is TK– and is also a deletant in respect of an essential viral glycoprotein, whereby the amplicon is necessary for the propagation of the helper virus when the preparation is grown on TK-cells in the presence of methotrexate.

15. The preparation according to claim 13 wherein the genes of the helper virus and of said herpesvirus amplicon taken together are defective in respect of an essential viral gene function.

16. The preparation according to claim 15, wherein the amplicon carries an inserted first essential viral gene, the helper virus is a deletant in respect of the corresponding first essential viral gene and is also a deletant in respect of a second essential viral gene, whereby the amplicon is necessary for the propagation of the helper virus when the preparation is grown on cells complemented in respect of the function of the second essential viral gene.

17. The preparation according to claim 16, wherein the first essential viral gene encodes an essential viral glycoprotein and the second essential viral gene also encodes an essential viral glycoprotein (different from that encoded by the first essential viral gene); e.g. gD and gH respectively.

* * * * *

UNITED STATES PATENT AND TRADEMARK OFFICE
CERTIFICATE OF CORRECTION

PATENT NO.  : 5,928,913
DATED       : July 27, 1999
INVENTOR(S) : Efstathiou et al.

It is certified that error appears in the above-identified patent and that said Letters Patent is hereby corrected as shown below:

Column 8,
Line 57, error reads "45 kg" should read -- 45 kb --

Column 10,
Line 21, error reads "MCMP" should read -- MOMP --

Column 15,
Line 9, error reads "CO34+" should read -- CD34+ --

Column 16,
Line 14, error reads "downregulating" should read -- downregulatory --
Line 17, error reads "downregulating" should read -- downregulatory --
Line 30, error reads "gel" should read -- gH --

Column 22,
Line 65, error reads "1.:6" should read -- 1:6 --

Column 23,
Line 22, error reads "CMCSF" should read -- GMCSF --

UNITED STATES PATENT AND TRADEMARK OFFICE
CERTIFICATE OF CORRECTION

PATENT NO. : 5,928,913
DATED : July 27, 1999
INVENTOR(S) : Efstathiou et al.

It is certified that error appears in the above-identified patent and that said Letters Patent is hereby corrected as shown below:

<u>Column 24,</u>
Line 14, error reads "GH-CSF" should read -- GM-CSF --

Signed and Sealed this

Thirty-first Day of July, 2001

*Attest:*

*Attesting Officer*

NICHOLAS P. GODICI
*Acting Director of the United States Patent and Trademark Office*

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (iii) HYPOTHETICAL: NO (iii) ANTI-SENSE: NO (xi) SEQUENCE DESCRIPTION: SEQ ID NO: 1:

TCAAAGCTTA TGGCTTCGTA CCCCTGCCAT                  30

(2) INFORMATION FOR SEQ ID NO: 2:

(i) SEQUENCE CHARACTERISTICS:
      (A) LENGTH: 30 base pairs
      (B) TYPE: nucleic acid

```
            (C) STRANDEDNESS: single
            (D) TOPOLOGY: linear (iii) HYPOTHETICAL: NO (iii) ANTI-SENSE: NO (xi) SEQUENCE DESCRIPTION: SEQ ID NO: 2:

TCAGTTAACG GACCCCGTCC CTAACCCACG                                    30

(2) INFORMATION FOR SEQ ID NO: 3:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (iii) HYPOTHETICAL: NO (iii) ANTI-SENSE: NO (xi) SEQUENCE DESCRIPTION: SEQ ID NO: 3:

TCAGTTAACA GCCCCTCTTT GCTTTCCCTC                                    30

(2) INFORMATION FOR SEQ ID NO: 4:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (iii) HYPOTHETICAL: NO (iii) ANTI-SENSE: NO (xi) SEQUENCE DESCRIPTION: SEQ ID NO: 4:

TCAGAATTCG AGCAGCTCCT CATGTTCGAC                                    30

(2) INFORMATION FOR SEQ ID NO: 5:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (iii) HYPOTHETICAL: NO (iii) ANTI-SENSE: NO (xi) SEQUENCE DESCRIPTION: SEQ ID NO: 5:

TCAAAGCTTC TGCAGGGCGG CGGGTCGTGG                                    30

(2) INFORMATION FOR SEQ ID NO: 6:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (iii) HYPOTHETICAL: NO (iii) ANTI-SENSE: NO (xi) SEQUENCE DESCRIPTION: SEQ ID NO: 6:

TCAGTTAACG GACCCCGTCC CTAACCCACG                                    30
```